United States Patent [19]

Erskine

[11] Patent Number: 5,501,675
[45] Date of Patent: Mar. 26, 1996

[54] SAFETY CATHETER ASSEMBLY HAVING SAFETY STOP PUSH BUTTON

[75] Inventor: Timothy J. Erskine, Sandy, Utah

[73] Assignee: Becton, Dickinson and Company, Franklin Lakes, N.J.

[21] Appl. No.: 364,635

[22] Filed: Dec. 27, 1994

[51] Int. Cl.⁶ ..................................... A61M 5/00
[52] U.S. Cl. .................. 604/263; 604/264; 604/164; 604/165; 604/171; 128/919
[58] Field of Search ............................ 128/919; 604/157, 604/164, 165, 171, 181, 187, 192, 198, 263, 264, 268, 272

[56] References Cited

U.S. PATENT DOCUMENTS

| | | | |
|---|---|---|---|
| 3,605,743 | 9/1971 | Arce | 604/157 |
| 4,747,831 | 5/1988 | Kulli | 604/110 |
| 4,900,307 | 2/1990 | Kulli | 604/110 |
| 4,904,242 | 2/1990 | Kulli | 604/110 |
| 4,927,414 | 5/1990 | Kulli | 604/110 |
| 4,929,241 | 5/1990 | Kulli | 604/263 |
| 4,973,316 | 11/1990 | Dysarz | 604/198 X |
| 4,994,042 | 2/1991 | Vadher | 604/165 |
| 5,046,508 | 9/1991 | Weissler | 128/763 |
| 5,059,184 | 10/1991 | Dyke | 604/198 |
| 5,104,384 | 4/1992 | Parry | 604/192 |
| 5,127,905 | 7/1992 | Lemieux | 604/164 |
| 5,129,884 | 7/1992 | Dysarz | 604/164 |
| 5,330,432 | 7/1994 | Yoon | 604/164 |
| 5,360,408 | 11/1994 | Vaillancourt | 604/198 |

Primary Examiner—Corrine M. Maglione
Assistant Examiner—N. Kent Gring
Attorney, Agent, or Firm—Eric M. Lee

[57] ABSTRACT

A safety stop push button mechanism is disclosed that prevents unwanted activation of the push button. The safety stop push button has particular applicability to a catheter and spring activated safety introducer needle assembly. A projection extending from the activation latch engages the catheter hub to prevent inadvertent activation of the safety mechanism until the catheter has been at least partially advanced distally over the needle.

14 Claims, 5 Drawing Sheets

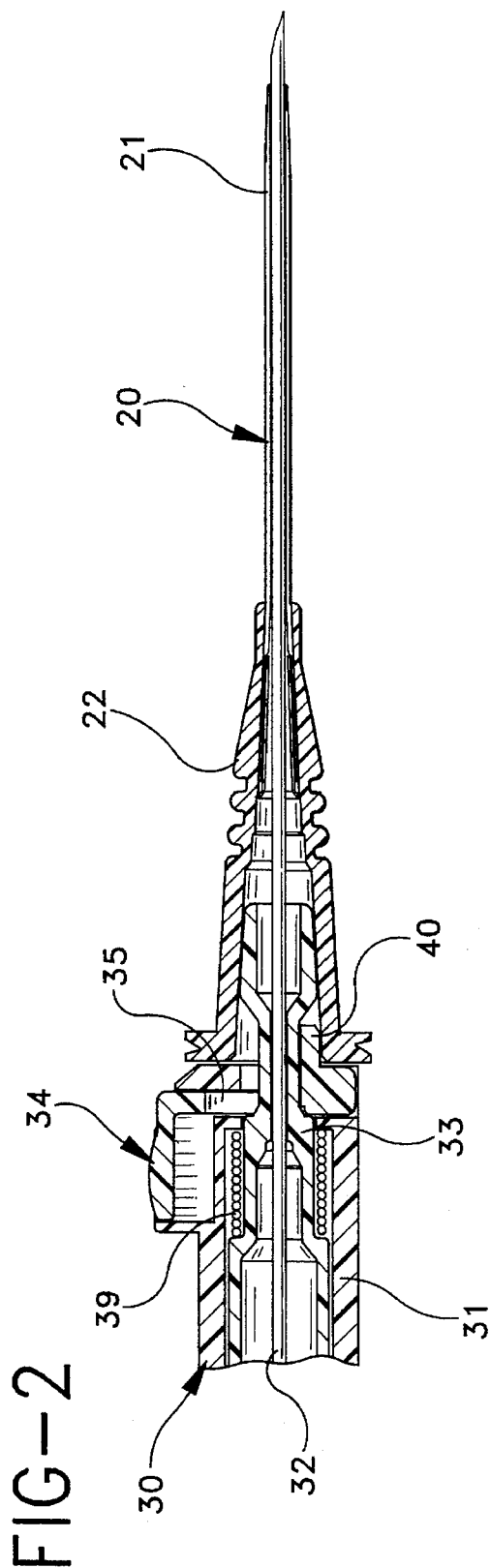
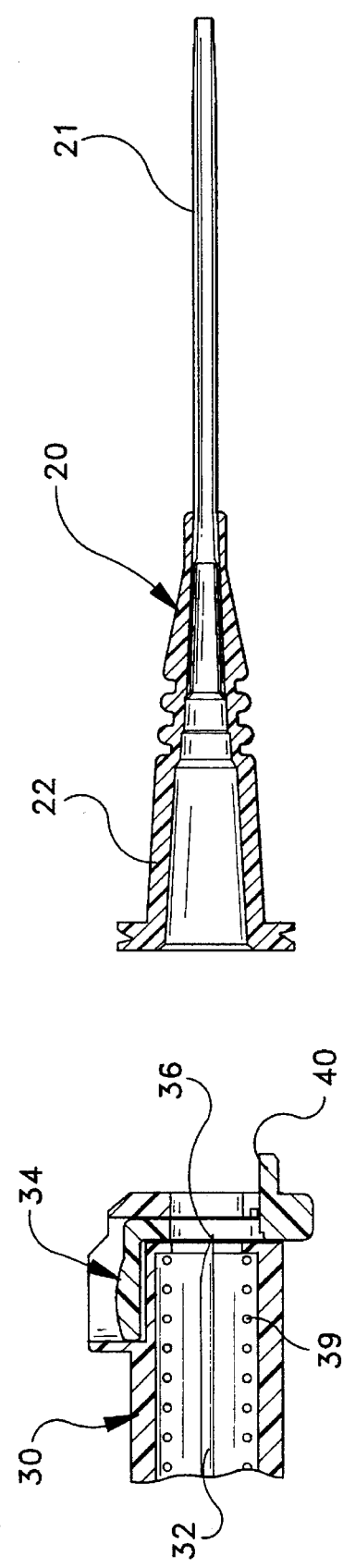

5,501,675

SAFETY CATHETER ASSEMBLY HAVING SAFETY STOP PUSH BUTTON

BACKGROUND OF THE INVENTION

This invention relates generally to a safety stop push button feature that could be used on most any push button activation mechanism to prevent unwanted activation of the push button. This invention has particular applicability for use in a spring actuated safety introducer needle assembly which may be used with an intravenous (IV) catheter.

With the advent of acquired immune deficiency syndrome (AIDS) and other infectious diseases, there has been much concern with accidental needle sticks of healthcare workers by used IV catheter introducer needles. As a result many companies have attempted to develop a safety needle system that would allow the healthcare worker to shield the sharp distal tip of the needle after the catheter has been placed in a patient's vein. One such system is shown in U.S. Pat. No. 4,747,831, the disclosure of which is hereby incorporated by reference.

In that system, the needle hub and introducer needle are slidably disposed in a hollow barrel with the sharp distal tip of the needle initially extending beyond the distal end of the barrel. A spring is located between the needle hub and the distal end of the barrel. A latch is used to keep the needle hub adjacent to the distal end of the barrel so the sharp distal tip of the needle extends beyond the distal end of the barrel. After the introducer needle and catheter have been properly inserted into the patient's vein, the latch is activated allowing the spring to force the needle hub to the proximal end of the barrel. As a result, the sharp distal tip of the needle is withdrawn into the barrel out of reach of the healthcare worker.

Although the above described device works for its intended purpose, it could be improved. Since the device is spring activated, movement of the latch will allow the spring to withdraw the needle into the barrel. Unfortunately, in certain circumstances, the healthcare worker may inadvertently depress the latch prior to the catheter being properly placed in the patient's vein.

SUMMARY OF THE INVENTION

It is therefore an object of this invention to provide a safety stop push button feature that can be used to prevent unwanted activation of the push button.

It is another object of this invention to provide a mechanism for minimizing the chances that a spring activated catheter and safety needle assembly will be inadvertently activated.

This invention includes an activation latch that extends across the lumen of the barrel and has a keyhole shaped opening therein. The needle and needle hub extend through this keyhole shaped opening. The smaller portion of the keyhole shaped opening engages the needle hub and allows the needle to be maintained in a position with the sharp distal tip extending out of the distal end of the barrel. When the latch is depressed, the larger portion of the keyhole shaped opening is aligned with the needle hub allowing the spring to push the needle toward the proximal end of the barrel and withdraw the sharp distal tip of the needle into the barrel. A projection extends from the latch toward the catheter hub. When the latch is engaged with the needle hub, the projection is adjacent to the catheter hub. The projection is located on the latch to prevent the latch from being depressed when the projection is located adjacent to the catheter hub. Thus, until the catheter is advanced distally over the needle, the latch cannot be activated.

The above and other objects and advantages will be apparent upon consideration of the following drawings and detailed description.

DESCRIPTION OF THE DRAWINGS

The preferred embodiments are illustrated in the appended drawings in which like reference numerals refer to like elements and in which:

FIG. 2 is a cross sectional view taken along line 2—2 of FIG. 1 prior to activation of the spring mechanism;

FIG. 3 is a cross-sectional view similar to the view shown in FIG. 2 but with the catheter advanced distally with respect to the introducer needle assembly and the spring activated and the needle withdrawn in the barrel;

DETAILED DESCRIPTION OF THE INVENTION

Although this invention is described in connection with a spring activated needle retraction system, it is to be understood that the safety stop push button could be used on other devices to prevent unwanted activation of the push button.

Figure 1:
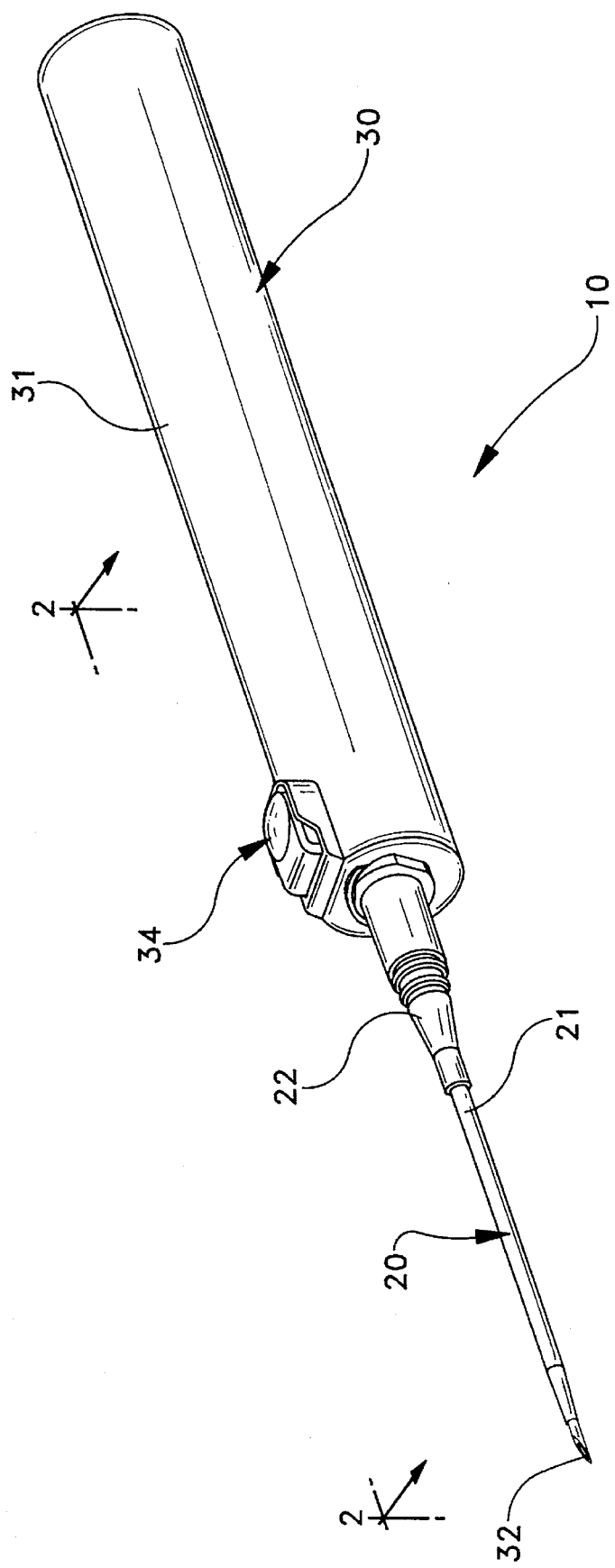
FIG. 1 is a perspective view of the catheter and safety introducer needle of this invention.
Figure 4:
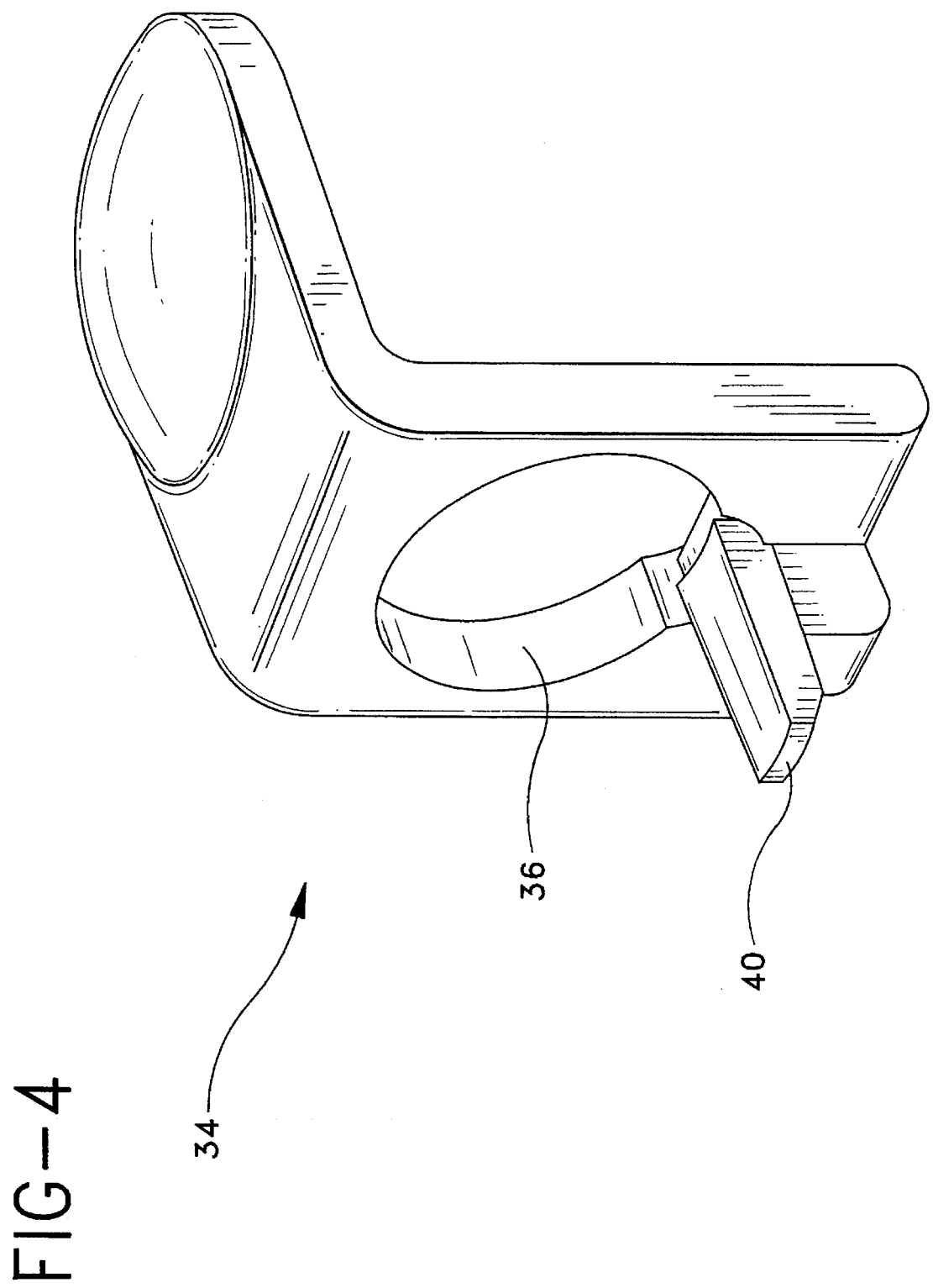
FIG. 4 is a perspective view of the latch and the preferred embodiment of the projection of this invention.

The catheter 20 and safety introducer needle assembly 10 are shown in FIG. 1. The catheter 20 has a tube 21 which is affixed to a catheter hub 22. The safety introducer needle assembly 30 includes a handle or barrel 31 a needle 32 a carrier or needle hub 33, a spring 39 and an activation latch 34. Spring 39 is located about needle 32 and needle hub 33 and extends between needle hub 33 and the distal end of barrel 31. Activation latch 34 extends into barrel 31 via a slot 35 formed in barrel 31 adjacent to the distal end. Activation latch 34 includes a keyhole shaped opening 36 that allows needle 32 and needle hub 33 to extend through activation latch 34. Activation latch 34 also includes a projection 40 that extends toward the distal end of catheter 20 and safety introducer needle assembly 10.

When activation latch 34 is "up" in the non-activated position, the smaller portion of keyhole shaped opening 36 is in communication with the barrel lumen. In this position, the smaller opening engages needle hub 33 and holds needle hub 33 adjacent to the distal end of barrel 31 against the force of spring 39. Preferably, needle hub 33 has a generally hour-glass shape so that its medial portion has a smaller diameter than either end. This shape facilitates engagement between the smaller opening in keyhole shaped opening 36 of activation latch 34 and needle hub 33. When activation latch 34 is in the non-activated position, projection 40 is located inside catheter hub 22. Thus, when catheter 21 is still located on needle 32 with catheter hub 22 adjacent to the distal end of barrel 31, projection 40 prevents activation latch 34 from being moved "down" into the activated position. Preferably, projection 40 has a length of between about 0.5 mm and about 2.5 mm. The actual length used should be long enough so projection 40 engages catheter hub 22 when catheter hub 22 is adjacent to the distal end of barrel 31. However, projection 40 should not be so long that it interferes with the use of catheter 20 and introducer needle 32.

When catheter 20 is moved off needle 32 so catheter hub 22 is not adjacent to the distal end of barrel 31, activation latch 34 can be moved "down," i.e. activated, because catheter hub 22 no longer interferes with the movement of projection 40. In this position, the larger opening of keyhole shaped opening 36 no longer engages needle hub 33. The larger opening of keyhole shaped opening 36 should be larger than the maximum diameter of needle hub 33. Spring 39 can thus force needle hub 33 to the proximal end of barrel 31 and withdraw the sharp distal tip of needle 32 into barrel 31.

Figure 7:
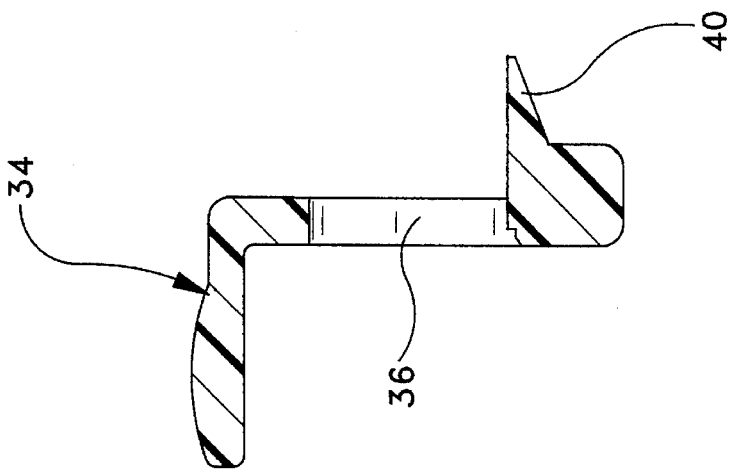
FIG. 7 is a cross-sectional view of the latch and another embodiment of the projection of this invention.
Figure 6:
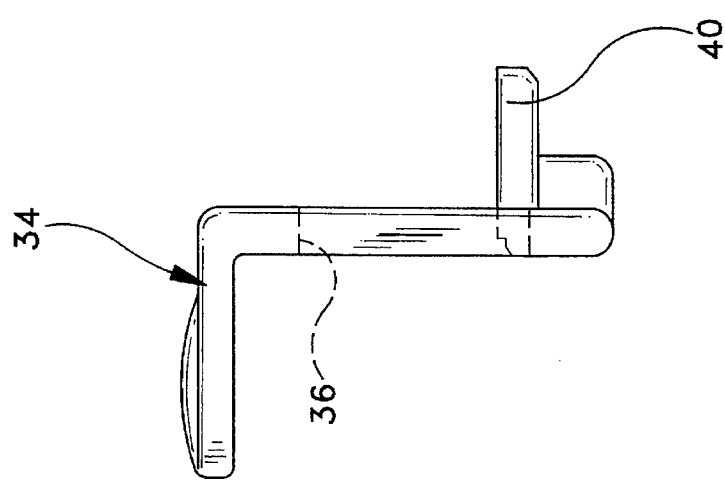
FIG. 6 is a side elevation view of the latch and the preferred embodiment of the projection of this invention.
Figure 5:
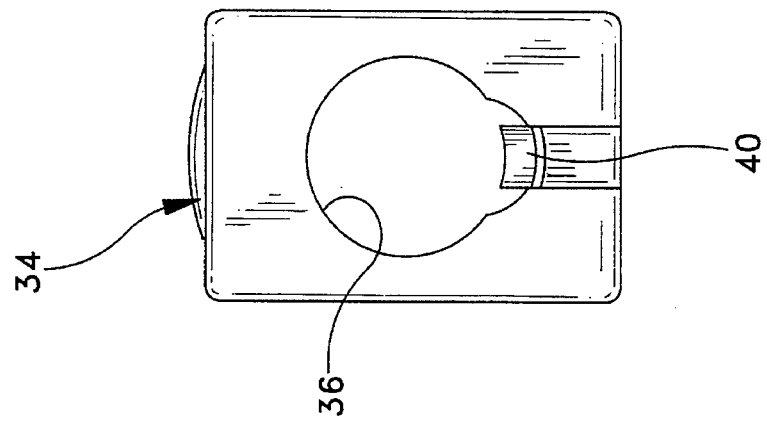
FIG. 5 is a front elevation view of the latch and the preferred embodiment of the projection of this invention.

Projection 40' on activation latch 34 can also be angled as shown in FIG. 7. This configuration allows the healthcare worker to activate activation latch 34 by pressing down firmly on activation latch 34. This downward force will transmit some axial force to catheter hub 22 because of the wedge shape of projection 40'. Catheter hub 22 will then be advanced in the distal direction clearing the way for complete depression of activation latch 40'. The wedge should be at an angle of between about 15 degrees and about 25 degrees to the longitudinal axis of catheter hub 22. Preferably this angle should be about 20 degrees.

Figure 8:
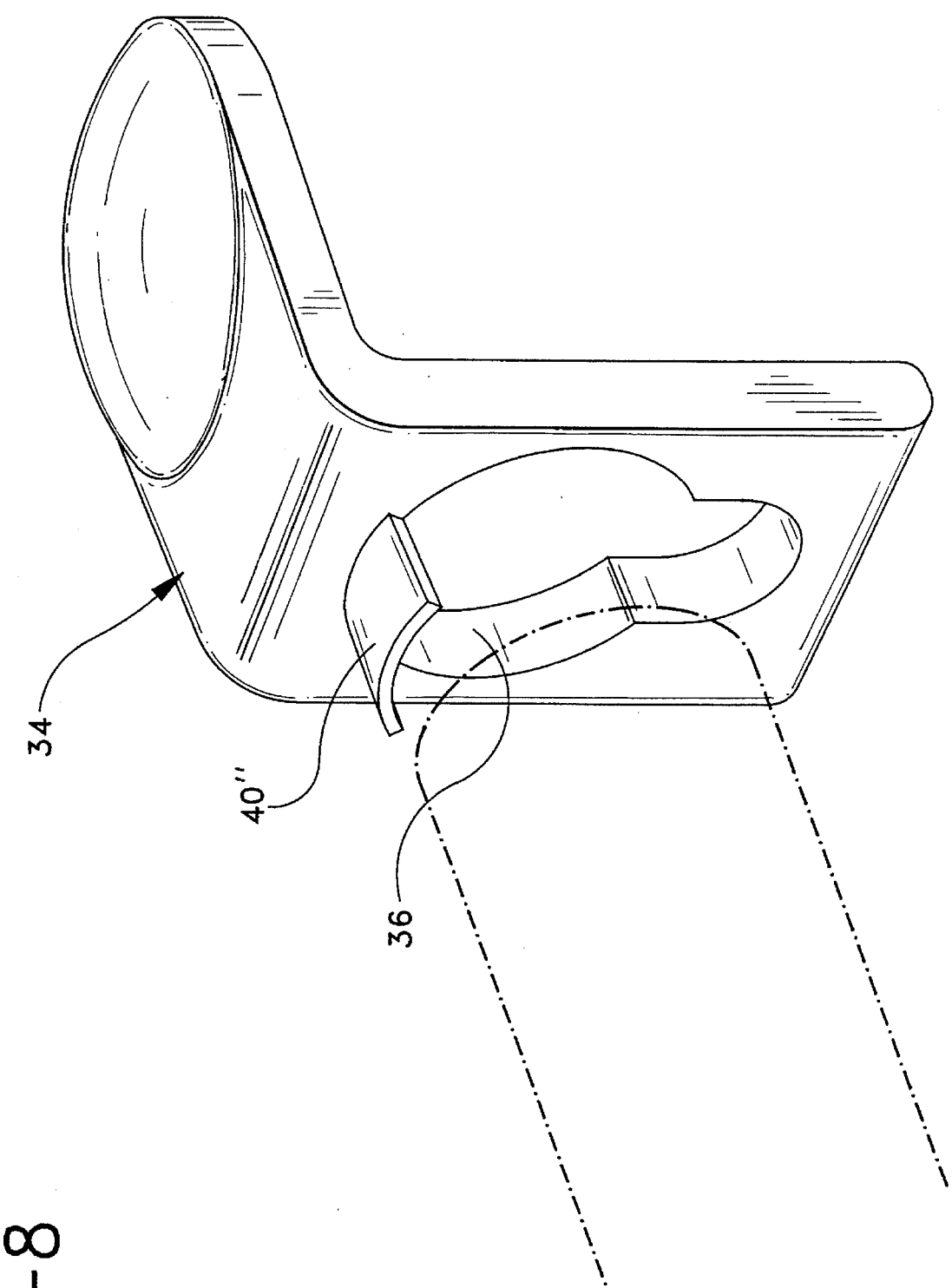
FIG. 8 is a perspective view of the latch and yet another embodiment of the projection of this invention.

Projection 40" can also be located adjacent to the top of keyhole shaped opening 36 as shown in FIG. 8. In this position, projection 40" engages the outside of catheter hub 22 to prevent downward movement of activation latch 34 when catheter hub 22 is adjacent to the distal end of barrel 31.

Thus it is seen that a safety stop push button mechanism is provided that prevents unwanted activation of the push button. For example, a spring activated catheter and safety introducer needle assembly is provided that minimizes the chances of inadvertent retraction of the needle into the barrel.

I claim:

1. A catheter and safety introducer needle assembly, comprising:

a catheter having a catheter hub with an inside and an outside;

a generally hollow barrel having a proximal end and a distal end;

a needle having a sharp distal tip and a proximal end;

a needle hub affixed adjacent to the proximal end of the needle and movably disposed in the barrel;

a spring disposed about the needle and extending between the needle hub and the distal end of the barrel;

an activation latch having a top and a bottom and movably mounted adjacent to the distal end of the barrel and adapted for selective engagement with the needle hub to hold the needle hub adjacent to the distal end of the barrel against the bias of the spring such that the needle extends beyond the distal end of the barrel and through the catheter with the catheter hub adjacent to the distal end of the barrel; and a projection extending from the activation latch for engagement with the catheter hub to prevent movement of the activation latch when the catheter hub is adjacent to the distal end of the barrel.

2. The catheter and safety introducer needle assembly of claim 1 wherein the projection has a length of between about 0.5 mm and about 2.5 mm.

3. The catheter and safety introducer needle assembly of claim 1 wherein the projection is wedge shaped.

4. The catheter and safety introducer needle assembly of claim 3 wherein the wedge shaped projection has a length of between about 0.5 mm and about 2.5 mm.

5. The catheter and safety introducer needle assembly of claim 3 wherein the wedge shaped projection extends at an angle of between about 15 degrees and about 25 degrees from an axis of the barrel.

6. The catheter and safety introducer needle assembly of either claim 1 or claim 2 wherein the projection is adjacent to the top of the activation latch for engagement with the outside of the catheter hub.

7. The catheter and safety introducer needle assembly of any of claims 1 through 5 wherein the projection is adjacent to the bottom of the activation latch for engagement with the inside of the catheter hub.

8. A medical device, comprising:

a handle having a proximal end and a distal end;

a carrier disposed in the handle for movement with respect to the handle;

a hub having an inside and an outside movably mounted to the distal end of the handle;

an activation latch having a top and a bottom, the activation latch movably mounted with respect to the handle and adapted for selective engagement with the carrier to hold the carrier adjacent to the distal end of the handle; and a projection extending from the activation latch for engagement with the hub to prevent movement of the activation latch when the hub is to the distal end of the handle.

9. The medical device of claim 8 wherein the projection has a length of between about 0.5 mm and about 2.5 mm.

10. The medical device of claim 8 wherein the projection is wedge shaped.

11. The medical device of claim 10 wherein the wedge shaped projection has a length of between about 0.5 mm and about 2.5 mm.

12. The medical device of claim 10 wherein the wedge shaped projection extends at an angle of between about 15 degrees and about 25 degrees from an axis of the handle.

13. The medical device of either claim 8 or claim 9 wherein the projection is adjacent to the top of the activation latch for engagement with the outside of the hub.

14. The medical device of any of claims 8 through 12 wherein the projection is adjacent to the bottom of the activation latch for engagement with the inside of the hub.

* * * * *